US007643882B2

(12) United States Patent
Boston

(10) Patent No.: US 7,643,882 B2
(45) Date of Patent: Jan. 5, 2010

(54) TREMOR REDUCTION SYSTEMS SUITABLE FOR SELF-APPLICATION AND USE IN DISABLED PATIENTS

(76) Inventor: Leon Boston, 3700 S. Plaza Dr., Suite F202, Santa Ana, CA (US) 92704

(*) Notice: Subject to any disclaimer, the term of this patent is extended or adjusted under 35 U.S.C. 154(b) by 610 days.

(21) Appl. No.: 11/441,404

(22) Filed: May 24, 2006

(65) Prior Publication Data

US 2007/0123951 A1 May 31, 2007

Related U.S. Application Data

(60) Provisional application No. 60/683,790, filed on May 24, 2005.

(51) Int. Cl.
*A61N 1/36* (2006.01)

(52) U.S. Cl. ......................... 607/48; 607/149; 600/386; 600/595

(58) Field of Classification Search .................... 607/48
See application file for complete search history.

(56) References Cited

U.S. PATENT DOCUMENTS 3,610,250 A 10/1971 Sarbacher
4,432,368 A * 2/1984 Russek ....................... 600/382
4,583,547 A 4/1986 Granek et al.
4,622,973 A * 11/1986 Agarwala .................... 607/48
4,697,808 A 10/1987 Larson et al.
4,817,628 A * 4/1989 Zealear et al. .............. 600/554
4,867,166 A * 9/1989 Axelgaard et al. .......... 600/391
4,919,148 A 4/1990 Muccio
5,070,873 A * 12/1991 Graupe et al. ................. 607/48
5,293,879 A * 3/1994 Vonk et al. .................. 600/595
5,330,516 A * 7/1994 Nathan ........................ 607/48
5,397,338 A * 3/1995 Grey et al. .................. 607/115
5,443,494 A * 8/1995 Paolizzi et al. .............. 607/149
5,487,759 A * 1/1996 Bastyr et al. ................ 607/149
5,562,707 A 10/1996 Prochazka et al.
5,643,332 A * 7/1997 Stein ........................... 607/49
5,766,236 A 6/1998 Detty et al.
6,282,448 B1 * 8/2001 Katz et al. .................... 607/48
6,496,739 B2 12/2002 Arbel
6,507,757 B1 * 1/2003 Swain et al. .................. 607/49
6,516,289 B2 2/2003 David
6,704,603 B1 3/2004 Gesotti
6,728,577 B2 4/2004 Minogue et al.
6,788,976 B2 9/2004 Gesotti
6,829,510 B2 * 12/2004 Nathan et al. ............... 607/149
6,839,594 B2 * 1/2005 Cohen et al. .................. 607/48

(Continued)

*Primary Examiner*—Kennedy J Schaetzle
(74) *Attorney, Agent, or Firm*—Dekel Patent Ltd.; David Klein

(57) ABSTRACT

A system and apparatus for enabling independent, highly reliable and accurate self-application of an anti-tremor means by a disabled patient, without requirement for application fixtures, wherein anti-tremor means comprises a single unit, self adhesive stimulation and recording electrode with an integrated supply of energy and a control unit, further comprising an alignment, and application means for applying said anti-tremor means configured to enable independently self application by a severely handicapped patient, wherein system and method for tremor reduction is by means of closed-loop functional electrical stimulation, including a sensor for sensing muscle movements, and Functional Electrical Stimulation (FES) apparatus for providing FES to a muscle, the FES apparatus being in communication with the sensor via a band pass filter for filtering around a tremor frequency to ignore slow movements and high frequency noise.

8 Claims, 5 Drawing Sheets

U.S. PATENT DOCUMENTS 6,885,896 B2 4/2005 Minogue et al.
7,149,582 B2 * 12/2006 Dar et al. ...................... 607/48
7,162,305 B2 * 1/2007 Tong et al. .................... 607/48
2002/0077689 A1 6/2002 Kirkland
2007/0106343 A1 * 5/2007 Monogue et al. .............. 607/48

* cited by examiner

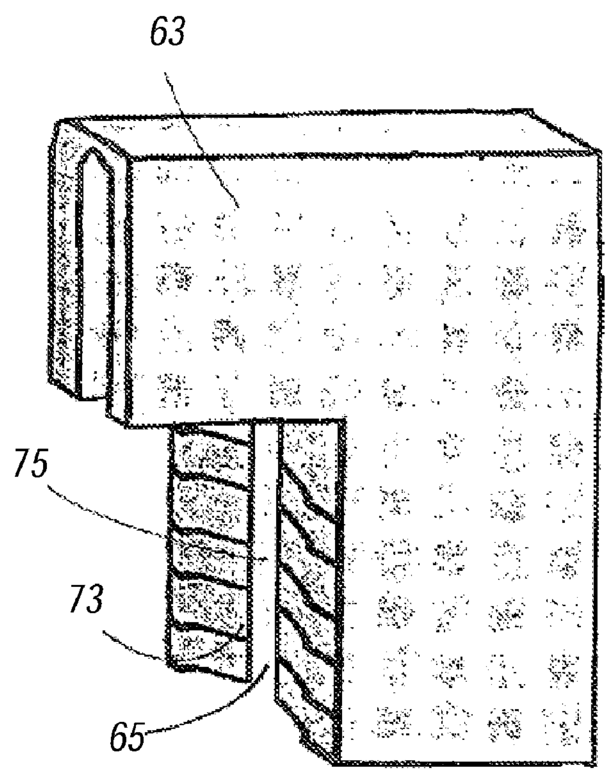
FIG. 2
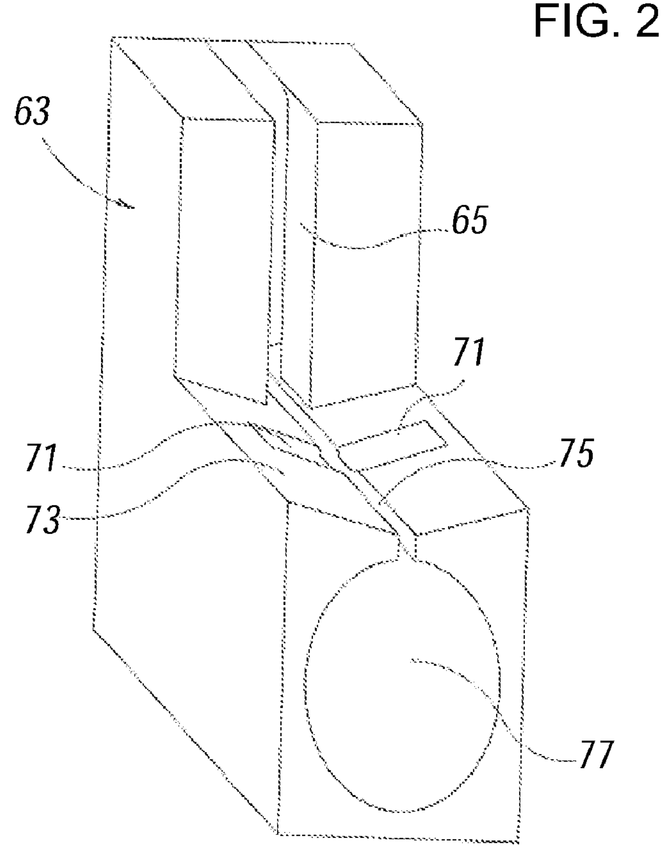

TREMOR REDUCTION SYSTEMS SUITABLE FOR SELF-APPLICATION AND USE IN DISABLED PATIENTS

PRIORITY DOCUMENT

The present application claims priority to the previously filed provisional patent application No.: 60/683,790 filed on May 24, 2005.

FIELD OF THE INVENTION

The present invention generally relates to a bio-electrical device and system. More specifically, the present invention relates to an apparatus, system and method for reducing deleterious involuntary tremors in the human body. The apparatus, system and method are especially configured to enable self application by a disabled patient, as well as to allow a physically impaired patient to independently prepare the device for repeated application and use.

BACKGROUND OF THE INVENTION

Deleterious tremors and involuntary motions of various parts of the human body pose a considerable health problem and result in substantial loss of quality of life. The impairment of proper motor function resulting from such deleterious tremors and involuntary motions have far reaching consequences for the sufferer, which include interference with basic normal motor function which may be grossly incapacitating.

Both volitional and involuntary movement of any given body region are brought about by the action of muscle contraction and relaxation, which in all cases is endogenously neurally mediated. Inappropriately coordinated muscle activity results in the abnormal movements characterizing these disorders.

An artificial way of causing muscle contraction, which may effectively override the natural neuro-muscular mechanism, is by way of intra-muscular or body surface application of externally applied electrical stimulation to activate motor nerves.

This type of artificially induced muscle activity has been used to treat tremors and the like by the appropriately tined selective stimulation of muscles to counterbalance the undesirable activity, and thus eliminate the deleterious motion.

This method is most effective when used in combination with a means of providing feedback as to the state of motion of the body part being treated, and computer based control means for subsequently regulating stimulation so as to achieve the desired clinical effect.

If for example a subjects arm is being treated, then feedback of the arm's motion can be used to control the mode, magnitude and site of electrical stimulation, based on the feedback detection and control system. Likewise, endogenous neural activity, detectable by conventional means, can be used for providing feedback for applied electrical stimulation, either independently or in combination with motion as mentioned above.

U.S. Pat. No. 5,562,707 issued to Prochazka et al, discloses a feedback mediated system for ameliorating deleterious tremors and involuntary motions, as broadly described above.

However, a problem exists wherein the traditional prior art lacks a suitable method for enabling the handicapped patient to independently apply the treatment system in a sufficiently accurate way to allow the system to perform reliably and reproducibly, given the motor skill limitations which the tremor condition imposes.

The Prochazka et al, patent, for example utilizes a glove like embodiment for applying the anti-tremor system to a patient, wherein multiple fixtures need to be engaged and then tightened in order to apply the device. The application of such an arrangement is further complicated due to the complex shape of the treatment device which requires correct initial placement even before the fixtures can be engaged and adjusted. Clearly, the practical usefulness of such a device for patients suffering from motor impairment is diminished in view of the relatively difficult application process required. Additionally, it would be problematic for a patient having involuntary motions and tremors to apply the device to themselves.

Another problem that exists in the prior art is the requirement for placement of the electrode-type device. Typically the patient has random tremors and involuntary bodily movements. The devices are most needed when the involuntary movements are most severe. The application of the electrode device to the needed body part can be inhibited because in order for the electrode device to accurately and effectively work, the device must be placed correctly. However, because of the involuntary movements, the patient often times is unable to correctly or accurately place the device on the needed site.

Further, even if the patient is able to properly fit the device on the site, typically the device will not work properly because of improper alignment with the muscle to be controlled.

A need therefore exists that provides a highly reliable and accurate method for applying an anti-tremor device. In addition, a need therefore exists for a apparatus, system and method for applying and delivering an anti-tremor device by a patient suffering from involuntary tremors and wherein the apparatus, system and method allows for correct, reliable and accurate placement of the device on the desired tremor location.

Additionally, a need exists for a apparatus, system and method for applying an anti-tremor device in a manner which requires the least possible motor skill. Moreover, a need therefore exists for an anti-tremor application with substantial improvements over the current state of the art, as will be described in detail below.

SUMMARY OF THE INVENTION

The present invention seeks to provide an effective apparatus, system and method for reducing tremors at a location on the body by means of a closed-loop functional electrical stimulation device. The closed-loop functional electrical stimulation device may be applied in a highly reliable and accurate manner by the patient requiring reduction of the involuntary movements, yet require the least possible motor skill for independent self application by handicapped patients. The invention is described for a single pair of muscles, but may be easily extended to a multiplicity of muscles.

To this end, in an embodiment of the present invention, an apparatus for enabling self-application of an anti-tremor means by a disabled patient is disclosed. The apparatus has a single unit stimulation and recording electrode with an integrated control means and an alignment and application means which is configured to enable independent application and use by said disabled patient.

In an exemplary embodiment, an apparatus for enabling self-application of an anti-tremor means by a disabled patient is disclosed wherein the single unit stimulation and recording electrode has an integrated control means wherein the single unit stimulation and recording electrode has a self adhesive thereon.

In an exemplary embodiment, an apparatus for enabling self-application of an anti-tremor means by a disabled patient is disclosed wherein the single unit stimulation and recording electrode has an integrated control means wherein the single unit stimulation and recording electrode has an internal power source contained thereon wherein the power source may be tuned off and on by the user.

In an exemplary embodiment, an apparatus for enabling self-application of an anti-tremor means by a disabled patient is disclosed wherein the alignment and application means is configured to allow the disabled patient to enter a body part into the application means for attachment of the stimulation electrode to the body part.

In an exemplary embodiment, an apparatus for enabling self-application of an anti-tremor means by a disabled patient is disclosed wherein a power supply means is contained within the electrode unit.

In an exemplary embodiment of the present invention, an apparatus for enabling self-application of an anti-tremor means by a disabled patient is disclosed. The apparatus has an an alignment application unit having a narrow pathway extending from an outside surface of the alignment application unit to an interior portion of the alignment application unit. Additionally the apparatus has an electrode application niche contained in the interior portion of the alignment application unit for placement of the electrode within the application unit.

In an exemplary embodiment, an apparatus for enabling self-application of an anti-tremor means by a disabled patient is disclosed wherein the alignment application unit has a channel for insertion of the patient's body part into the application unit.

In an exemplary embodiment, an apparatus for enabling self-application of an anti-tremor means by a disabled patient is disclosed wherein the alignment application unit has sponge walls.

In an exemplary embodiment, an apparatus for enabling self-application of an anti-tremor means by a disabled patient is disclosed wherein the alignment application unit has a cylindrical cavity wherein the cylindrical cavity receives the body part of the user when inserted into the alignment application unit.

In an exemplary embodiment, an apparatus for enabling self-application of an anti-tremor means by a disabled patient is disclosed wherein the alignment application unit has a niche wherein the niche has an attachment means. The niche contains an electrode complex therein which may be attached thereto for proper alignment with the inserted body part of the user.

In an exemplary embodiment of the present invention, an apparatus for enabling self application of anti-tremor means by a disabled patient is disclosed. The apparatus has a sensor for sensing muscle movements and a functional electrical stimulation (FES) apparatus for providing FES to a muscle. The FES apparatus communicates with the sensor via a band pass filter for filtering around a tremor frequency to ignore slow movements and high frequency noise.

In an exemplary embodiment, an apparatus for enabling self-application of an anti-tremor means by a disabled patient is disclosed wherein an accelerometer is disclosed to measure the acceleration of the arm and muscle movement.

In an exemplary embodiment, an apparatus for enabling self-application of an anti-tremor means by a disabled patient is disclosed wherein a microprocessor is disclosed to analyze the data received from the functional electric stimulation apparatus for proper response to involuntary movement in a patient.

In an exemplary embodiment, an apparatus for enabling self-application of an anti-tremor means by a disabled patient is disclosed wherein a microprocessor is disclosed that utilizes calibration algorithms to determine stimulation feedback and movements relating to the functional electrical stimulation apparatus.

In an embodiment of the present invention, a system for enabling self application of anti-tremor means by a disabled patient is disclosed. The system has a single unit stimulation and recording electrode with an integrated control means. Additionally the system has an alignment and application means which is configured to enable independent application and use by said disabled patient. Moreover, the system has an alignment application unit having a narrow pathway extending from an outside surface of the alignment application unit to an interior portion of the alignment application unit. Further, the system has an electrode application niche contained in the interior portion of the alignment application unit for placement of the electrode within the alignment application unit. Moreover, the system has a sensor for sensing muscle movements and a functional electrical stimulation (FES) apparatus for providing FES to a muscle, the FES apparatus being in communication with said sensor via a band pass filter for filtering around a tremor frequency to ignore slow movements and high frequency noise.

In an embodiment of the present invention, a method for enabling self application of anti-tremor means by a disabled patient, the method comprising the steps of: providing a self adhesive single unit stimulation and recording electrode with an integrated control means; providing an alignment and application means which is configured to enable independent application and use by said disabled patient wherein the alignment application unit has a narrow pathway extending from an outside surface of the alignment application unit to an interior portion of the alignment application unit; and placing an electrode application niche in the interior portion of the alignment unit for placement of the electrode within the alignment application unit.

In an exemplary embodiment, the method for enabling self-application of anti-tremor means further comprises the step of: allowing the patient to place the affected body part into the narrow pathway of the alignment application unit.

In an exemplary embodiment, the method for enabling self-application of anti-tremor means further comprises the step of: allowing the self adhesive single unit stimulation and recording electrode to contact with the affected body part in the interior portion of the alignment application unit.

In an exemplary embodiment, the method for enabling self-application of anti-tremor means further comprises the step of: placing a sensor for sensing muscle movements on the patients affected body part.

In an exemplary embodiment, the method for enabling self-application of anti-tremor means further comprises the step of: attaching the electrode to the external body part of the patient In an exemplary embodiment, the method for enabling self-application of anti-tremor means further comprises the step of: allowing for easy removal of the electrode by the use of a liquid thereon.

In an exemplary embodiment, the method for enabling self-application of anti-tremor means further comprises the step of: providing a power supply means whereby the electrode may be activated and deactivate by the user when needed.

In an exemplary embodiment, the method for enabling self-application of anti-tremor means further comprises the step of: providing a Functional Electrical Stimulation (FES) apparatus for providing stimulation to a muscle wherein the FES apparatus is able to communicate with the electrode via a band pass filter for filtering around a tremor frequency to ignore slow movements and high frequency noise.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

The invention will now be illustrated by reference to the figures below.

FIGS. 2A and 2B show is a simplified illustration of an apparatus for effecting the proper alignment and application of a stimulation and/or recording electrode, in a user independent manner, in accordance with an embodiment of the present invention.

DETAILED DESCRIPTION OF THE EXEMPLARY EMBODIMENTS

Stimulation/Recording Electrode.

Figure 1A:
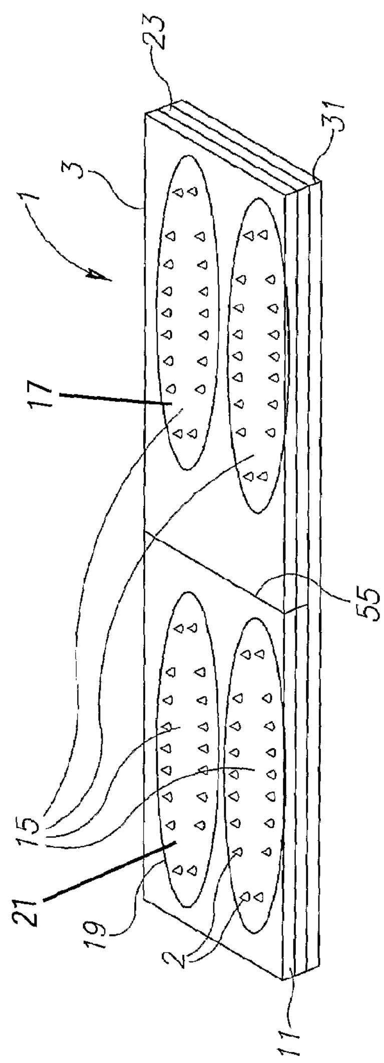
FIGS. 1A, 1B and 1C illustrate a stimulation and/or recording electrode in accordance with an embodiment of the present invention.
Figure 1B:
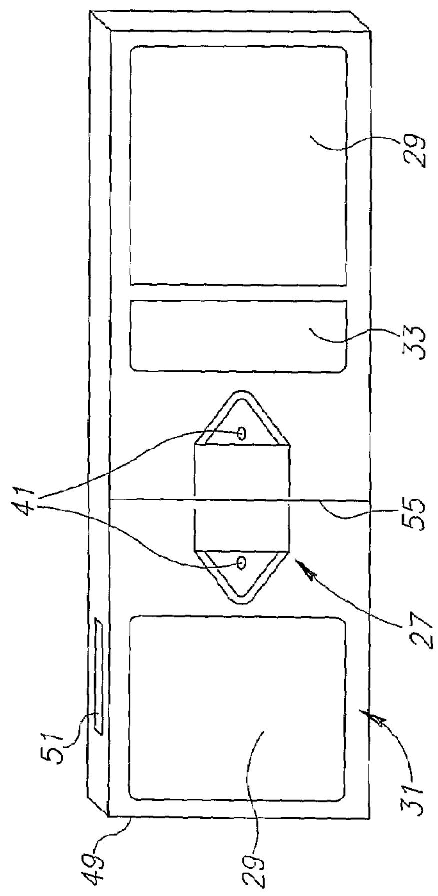
Figure 1C:
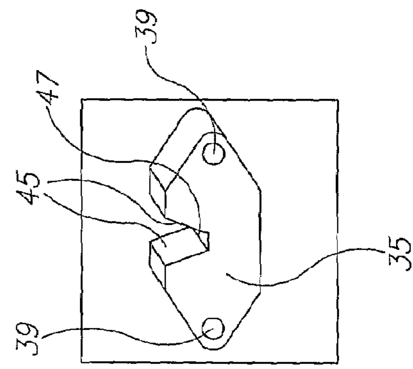

FIGS. 1A, 1B and 1C illustrates the stimulation/recording electrode unit 1 which is comprised of the following three thin layers:

The first layer is an adhesive and conductive interface layer 3 which directly interfaces with the skin surface 9. The first adhesive and conductive interface layer 3 provides the electrical contact necessary for the functions of conducting electrical energy to the skin surface 9 for effecting the muscle contraction (illustrated in FIG. 3), and for the detection of naturally occurring bio-potential signals such as the electromyographic (EMG) signals indicative of neuro-muscular activation.

The adhesive and conductive interface layer 3 in an exemplary embodiment may be composed of a hydrophyllic "hydrogel" material 11 of which there are many commercially available varieties.

The hydrorgel layer 11 may possess both strong adhesive properties as well as high electrical conductivity to facilitate the acquisition of bio-electrical signals from the body surface 9 as well as the application of the electrical stimulation.

The hydrogel surface 11 may be subdivided into electrically discrete regions 15 by creating gaps 17 in the hydrogel layer 11 so as to generate vacant perimeter borders 19 circumscribing electrically isolated regions 21, for the purpose of allowing selective stimulation and/or recording.

A second flexible conducting layer 23 is provided wherein the second flexible conducting layer 23 may channel the flow of electrons between the body surface 9 and the device's control system 27, described in greater detail below. The flexible conducting layer 23 may provide electrical contact between the skin surface 9 and the source of electromotive force (EMF) 29. Additionally, the flexible conducting layer 23 may provide a means for acquiring the bio-electrical signals. Moreover, the flexible conducting layer 23 may provide a means for connecting the skin contacting surface 9 to the control system 27 so as to allow appropriate electrical stimulation or recording of the bio-potential signals as determined by the control system 27. The flexible conducting layer 23 may be comprised for example of electrically conductive rubber, single or double sided flexible printed circuit board material or any other suitable electrical conducting means which possesses an appropriate degree of flexibility.

The third outer flexible layer 31 is provided on the stimulation recording electrode unit 1. The flexible outer layer 31 may serve as a source of electrical energy and also may serve as a protective covering layer. In an exemplary embodiment, a power source 33 may be contained thereon in the outer flexible layer 31. Many different types of power sources 33 may be utilized to power the electrode unit 1. In an exemplary embodiment of the present invention, so called "paper batteries" may be utilized to power the electrode unit 1. The outer flexible layer 31 may also serve as a portal for the placement of the re-usable control unit 27 which regulates the feedback controlled stimulatory activity as well as integrating the input information which will be described in greater detail below.

As further illustrated in the lower panel of FIG. 1C, an insertion portal 35 for the reusable control unit 27 is shown. FIG. 1B illustrates the manner in which the control unit 27 may interface between the respective outer flexible layer 3. As illustrated above, the outer flexible layer 3 may serve a reservoir of electrical energy and more specifically of the power source 33. Moreover, the outer flexible layer 31 may conduct with the flexible conducting layer 23 which interfaces between the stimulating and/or data acquiring electrodes 2 and the control unit 27. It should be noted that the portal 35 is designed to simplify insertion and orientation of the control unit 27, by virtue of a number of features including: a pair of magnets 39 for receiving magnets of opposite polarity 41 at corresponding positions 43 on the control unit 27, thus ensuring that inverse placement of the control unit 27 is impossible, and further ensuring that the control unit 27 is properly oriented with respect to the electrode unit 1. The portal 35 may also have conical side walls 45 of the insertion portal 47, and inverse slope of the control unit 27, to facilitate the smooth alignment of the control unit 27 with respect to the electrode unit 1 and a geometrical arrangement of the insertion portal 47, (and inverse geometry of the control unit 27), to ensure accurate placement of the control unit 27 with respect to the electrode unit 1.

Collectively, these features allows the control unit 27 to be placed roughly in the region of the insertion portion since the magnets 39 will then complete the positioning process and fix the control unit 27 accurately in place, such that the control unit 27 may be easily slid into the insertion portal 47 even in the presence of severe body tremors by the patient.

In an exemplary embodiment, a relatively large region, or even the entire external surface 49 of the multi-layer unit 1 may be configured to function as an on/off switch 51. This on/off switch 51 may be activated or deactivated by the patient simply pressing any portion of the external surface 49 of the electrode unit 1. In another exemplary embodiment, the electrode unit 1 may activated or deactivated by using a voice activated means (not shown) known to the art.

It is advantageous to the present invention to allow for removal of the multi-layer electrode unit 1 and allow for extraction of the re-usable control unit 27. In an exemplary embodiment of the present invention, the electrode unit 1 may be easily self-applied by a disabled patient (not shown), so too is it vital that it be equally easily removed. Although it would be relatively easy for many patients to simply pull the device 1 off, for those unable to do so it would be possible to place the application site under a steady and sustained stream of water. Since the adhesive layer 3 is strongly hydrophyllic, it will after a time become water logged and lose its adhesiveness to the extent to which the stream of water can then dislodge it.

Extracting the re-usable control unit 27 can be easily achieved by simply folding the multi-layer electrode unit 1 along a prepared fault line 55 running through the mid point 57 of the control unit 27. Since the opposing sides of the hydrogel surface 3 retain a degree of adhesiveness after removal (even after the above described stream of water method), the act of folding the unit 1 along the fault line 55 will result in a bending moment strong enough to disrupt the magnet 29 contact which held the control unit 27 to the multi-layer unit 1.

The above described multi-layer electrode unit 1 may be characterized by having a high degree of flexibility to allow it to conform to the contour of the particular body surface region to which it is to be applied. The multi-layer electrode unit 1 may also be further characterized by being highly adhesive over its entire body contacting surface so that it readily adheres to the body surface and remains firmly attached to the intended site of application. Further features of the multi-layer electrode unit 1 may include a means for easily switching the unit 1 on or off, as well as simple means for removing the unit 1 and extracting the re-usable control unit 27.

The multi-layer electrode unit 1 in an exemplary embodiment may have a special arrangement of side mounted magnets 29 of like polarity, as shown in the lower panel of FIG. 1, for facilitating proper orientation of this unit 1 with respect to the opposite polarity at corresponding positions on an arm alignment and electrode application unit 63. The two units have corresponding magnets 29 opposing polarity, to ensure that inverse placement of the multilayer complex is impossible, and further ensuring that it is properly oriented with respect to the arm alignment and electrode application unit 1. Conical, or fluted side wall design of the insertion region of the arm alignment and electrode application unit 1, and inverse slope of the multi-layer unit, further facilitates smooth alignment between the two units.

Alternative methods for non-permanently fixing the multi-layer unit to the arm alignment and electrode application unit include; surface adhesive attachment, or "Velcro" attachment.

FIGS. 2A and 2B illustrates an apparatus 63 for effecting the proper alignment and application of a multi-layer stimulation and/or recording electrode I of the type described above, in an essentially user independent manner. For purposes of explanation the apparatus 63 is described for application to a patients arm, however it should be understood that application to other body sites is also possible.

The arm alignment and electrode application unit 63 may be intended to accurately and non-permanently tether the multi-layer stimulation and/or recording electrode unit 1, and to further set the correct arm orientation, so that the multi-layer unit 1 becomes correctly attached to the patients body surface to permit accurate and effective anti-tremor treatment.

As can be seen in FIGS. 2A and 2B, there is a narrow pathway 65 for the vertical insertion of the patients hand (not shown). The limited width 67 of this region ensures that the patient must position the hand with fingers outstretched and position the hand parallel to the axis of the vertical insertion pathway 65. This may ensure the correct orientation of the arm.

Another feature of the arm alignment and electrode application unit 63 is a special niche 71 for receiving the multi-layer unit 1. This niche 71 possesses magnets 29 corresponding to the position of the magnets 29 in the multi-layer unit 1 but of opposing polarity, to ensure that inverse placement of the multilayer complex is impossible, and to further ensuring that it is properly oriented with respect to the arm alignment and electrode application unit 1.

A conical, or fluted side wall 73 design of the insertion region of the arm alignment and electrode application unit 63, and inverse slope of the multi-layer unit 1, further facilitates smooth alignment between the two units for easy application by a handicapped patient. In practice, the multi-layer unit 1 needs only to be roughly placed in the region of niche 71 since the magnets 29 will then complete the positioning process and fix the multi-layer unit 1 accurately to the arm alignment and electrode application unit.

The correct distance between the finger tips and the multi-layer unit on the patients arm is determined by virtue of the multi-layer unit's 1 application niche's 71 distance from the side wall 73 being tailored to the patients arm size.

After the arm has passed through the insertion pathway 65, it will come into contact with the adhesive surface 3 of the previously placed multi-layer unit 1, placed at the insertion niche 71. The magnetic force holding the opposing ends of the multi-layer unit 1 in place provides sufficient resistance to cause the multi layer unit 1 to become properly adhered to the patients skin before it can become dislodged from the magnetic binding sites.

With further application of downward force, the patients arm, now with the multi-layer unit 1 at least partially attached, comes into contact with the upper side sponge walls 75 (alternatively formed of foam or other suitable compliant and elastic material), which apply even pressure to the electrode attaching it to skin surface as the arm is forces between the two sides and finally brought all the way into the sponge walled cylindrical cavity 77, of the arm alignment and electrode application unit 1. The cavity 77 is configured to snugly fit around the arms perimeter to apply gentle force to further ensure complete attachment of the multi-layer unit 1 to the patient.

Having finally brought the arm into cavity 77, the multi-layer unit 1 will have been completely attached to the treatment site, and thus the arm may be withdrawn from the unit 77 with the multi-layer unit 1 firmly in place in the optimal region for effecting the feedback controlled anti-tremor function soon to be described.

As can be appreciated from the above description, the combined use of the multi-layer unit 1 and the arm alignment and electrode application unit 63 facilitates the application of the anti-tremor means in a consistent manner, to ensure correct orientation and location. Furthermore, the foam housing provides support for trembling arm, obviates the need for the use of the second hand and causes minimal interference with blood circulation during the application process.

Thus, the application of the multi-layer unit 1 merely requires the patient to place the hand in the pathway 65, push the arm down and then remove the arm.

As can be understood, the above described multi-layer units 1 and arm alignment and electrode application units are effective for providing feedback controlled electrical stimulation to counteract abnormal tremor activity.

The successful performance of this goal is critically dependent on the accurate placement of the stimulation electrodes 1 in correct proximity to the appropriate muscles.

The following four parameters define the appropriate configuration of the multi-layer stimulation/recording unit for effecting appropriate treatment at differing body locations:

1. anatomical variations from body region to body region,
2. the side of the body being treated (left or right), and
3. size variation between patients.

The problem may be dealt with in the following ways;

1. anatomical variations between differing body regions may be dealt with by appropriately configuring the partitioning of stimulation/recording regions of the multi-layer unit 1 in accordance with the specific myology of the respective treatment sites, knowledge of which is well known to the medical literature,
2. similarly, the sidedness issue can be resolved by appropriately configuring the partitioning of the multi-layer unit 1 in accordance with the appropriate myology of the respective treatment sites, and finally,
3. size variation between patients can be addressed by appropriately
   - a), scaling the multi-layer unit 1 in accordance with the girth of the respective treatment sites (i.e. having various sized units to accommodate various size ranges), and
   - b), scaling the alignment and electrode application unit in accordance with the length of the respective treatment sites by placing the insertion niche 65 of the alignment and electrode application unit 63 an appropriate distance from the terminal extremity of the alignment and electrode application unit (i.e. having various lengths between these points), so that the multi-layer unit 1 is placed at the optimal position along the length of the given treatment site.

Figure 3:
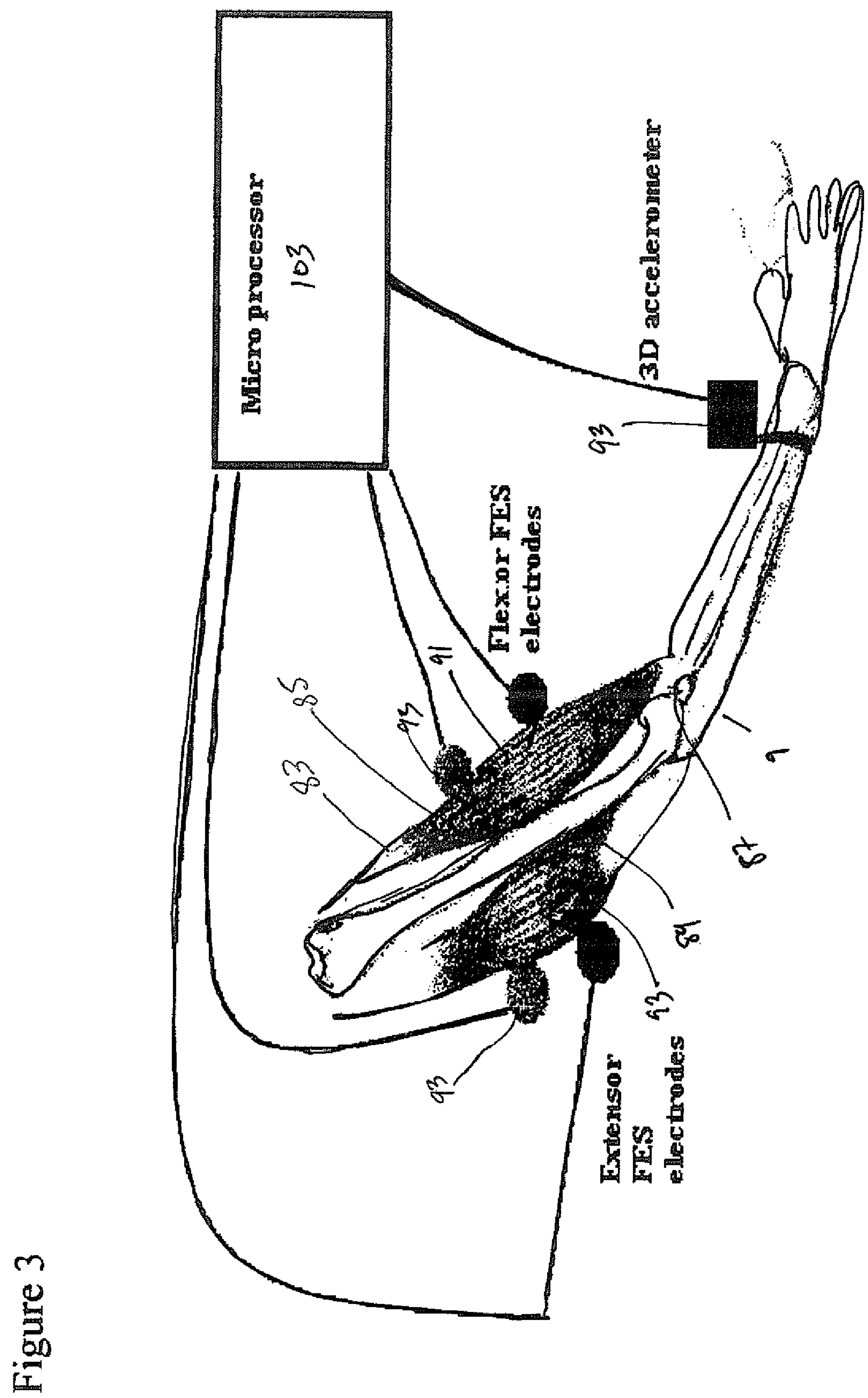
FIG. 3 is a simplified illustration of a system for tremor reduction by means of closed-loop functional electrical stimulation, in accordance with an embodiment of the present invention.

Reference is now made to FIG. 3, which illustrates a system for tremor reduction by means of closed-loop functional electrical stimulation 81, in accordance with an embodiment of the present invention.

The muscles of the upper arm 83 are an example of dual action muscles, antagonistic muscles, including a flexor 85, a muscle that bends a joint 87, and an extensor 89, a muscle that straightens a joint 87. When the biceps muscle 91 (on the front of the upper arm, flexor 85) contracts, it bends or flexes the elbow joint 87. When the triceps muscle 93 (on the back of the upper arm, extensor 89) contracts, it opens, or extends, the elbow joint 87.

A controlled movement requires contraction by both muscles 91, 93. A muscle pulls when it contracts, but exerts no force when it relaxes and cannot push. When one muscle pulls a bone in one direction, another muscle is needed to pull the bone in the other direction.

A normal characteristic of all skeleton muscles is that they remain in a state of partial contraction. At any given time, some muscles are being stimulated while others are not. This causes a tightened, or flexed, muscle and is known as muscle tone.

The closed loop tremor reduction system senses the overall movement of the arm that is composed of an intentional movement and tremor. Distinguishing between intentional movement and tremor is impossible unless one can guess what the patient's intentions are. Therefore we differentiate between "intentional" low pass signals (around <1 Hz) and high pass (around>1 Hz) signals. In general, the system ignores low pass movements and restrains high pass movements. One should note that the earth's gravity g—is a constant "low pass" factor that may be ignored.

The restrain of high pass movement is made by generating Functional Electrical Stimulation (FES) at the muscle that generates an opposite action. An accelerometer 93 may be used to measure the acceleration of the arm with electronic equipment 95. Most accelerometers 93 available for the measurements in biomechanics are extremely light and weigh a few grams. There are various types of accelerometers 93, including but not limited to, MEMS (micro-eletro-mechanical system), piezoresistive, strain gauge, piezoelectric, and inductive transducers. In a prototype of the invention, two ADXL202 low cost 2 g dual axis MEMS Accelerometers 93 may be used for three dimensional acceleration measurements. The ADXL202 allows bandwidth of about 50 Hz.

As is known in the art of measurement, there may be a small error in the measured acceleration, which is now discussed. The magnitude of the acceleration measured with an accelerometer 93 depends on various factors, e.g., bone acceleration, mounting interaction, angular motion and gravity. Accelerometers 93 are mounted by strapping them to the segment of interest at a location with minimal soft tissue between the accelerometer 93 and the bone of interest. In any mounting case, the acceleration measured represents not "the bone acceleration" but rather the acceleration of a specific mass element at the surface of the bone or even of a point outside the bone. Acceleration of a specific bone location can then be determined mathematically from several acceleration measurements or from additional measurements.

Acceleration measurements on a segment of the human body provide a signal which is composed of translational, rotational, and gravitational components. Accelerometers measured during human or animal locomotion have different combinations of the three acceleration components, depending on the actual movement. Functional Electrical Stimulation (FES) is a means of producing useful movement in muscles and is well known in the art. Electrical impulses are applied using either skin surface or implanted electrodes and course muscles to contract in a controlled manner. Applications are found in spinal cord injury, stroke, MS and cerebral palsy to assist standing, walking and hand function. The most common use for FES is a means of producing useful movement in paralyzed muscles. The tremor reduction system activates "free-run" rather than paralyzed muscles.

An electromyogram (EMG) represents the aggregate electrical activity produced by multiple action potentials that are generated by contracting muscle fibers. The EMG is not a regular series of waves like the ECG but a chaotic burst of overlapping high frequency signals (around 1 KHz) that are recorded using non-invasive electrodes 97. These bioelectrical signals are typically very small in amplitude (microvolts) and an amplifier is required to accurately record, display and analyze the EMG.

Figure 4:
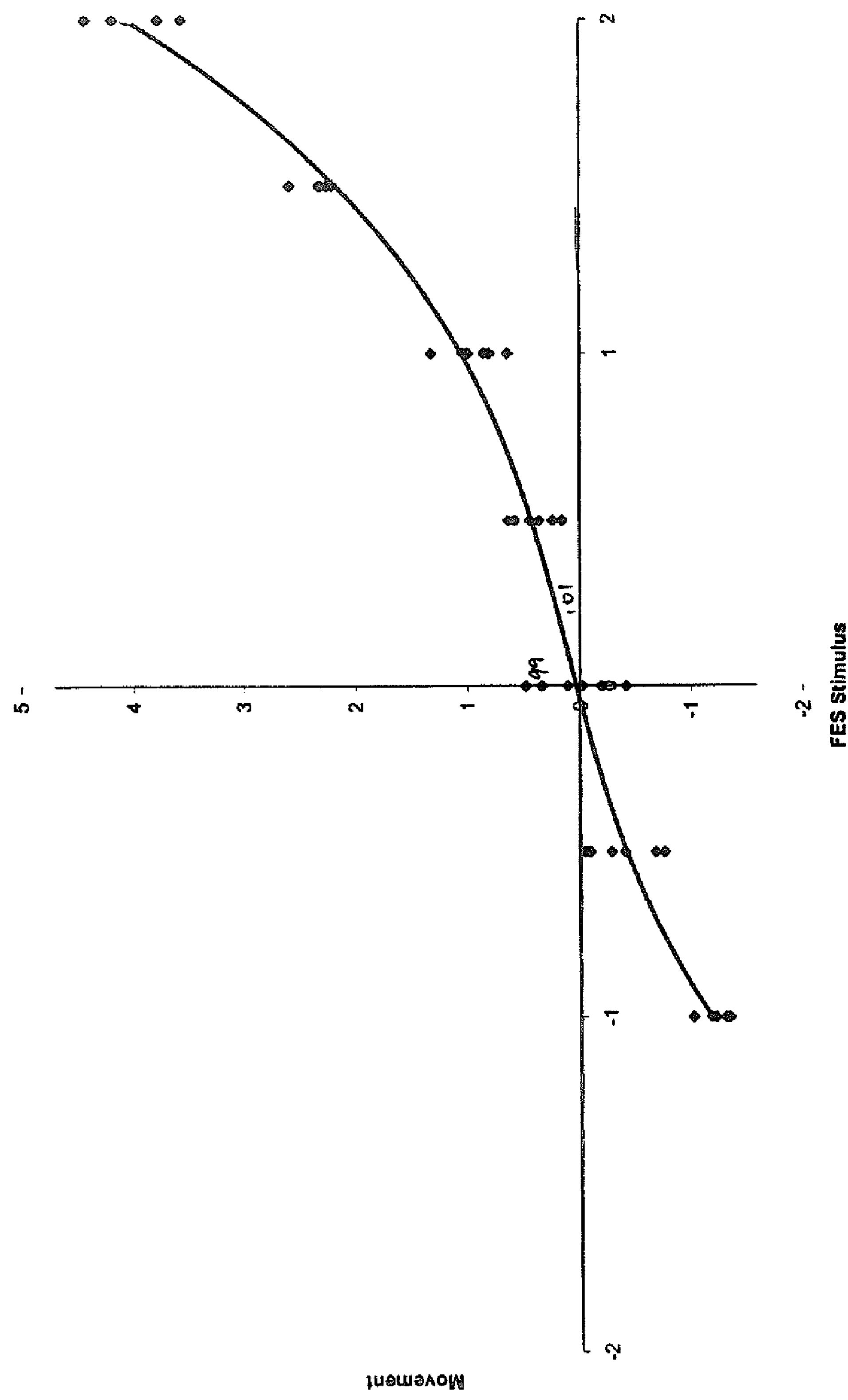
FIG. 4 is an exemplary graph of muscle movement as a function of Functional Electrical Stimulation (FES).

FIG. 4 further illustrates an exemplary graph of muscle movement as a function of FES. A stabilization algorithm may be used in the invention. The stabilization requires two concurrent tasks: calibration 99 and filtering 101. The system may be manually attached to the muscles using self adhesive electrodes and the accelerometers 93 may be attached using rubber bands (or Velcro). Due to the diverse possibilities of attachments the effect of the FES on hand movement should be calibrated.

Calibration may be performed in the beginning of device activation (initial calibration) and at run time (fine tuning). Calibration may be performed by collecting FES stimulation amplitude and movement response. Due to tremor, fluctuations are present at the movement axis. During initial calibration the statistics is built using full range tests initialized by the microprocessor 103. During run time the calibration 99 is slowly tuned to reflect small changes in electrode conductivity, accelerometer 93 movements, etc. The FES stimulus is limited for patient safety.

Figure 5:
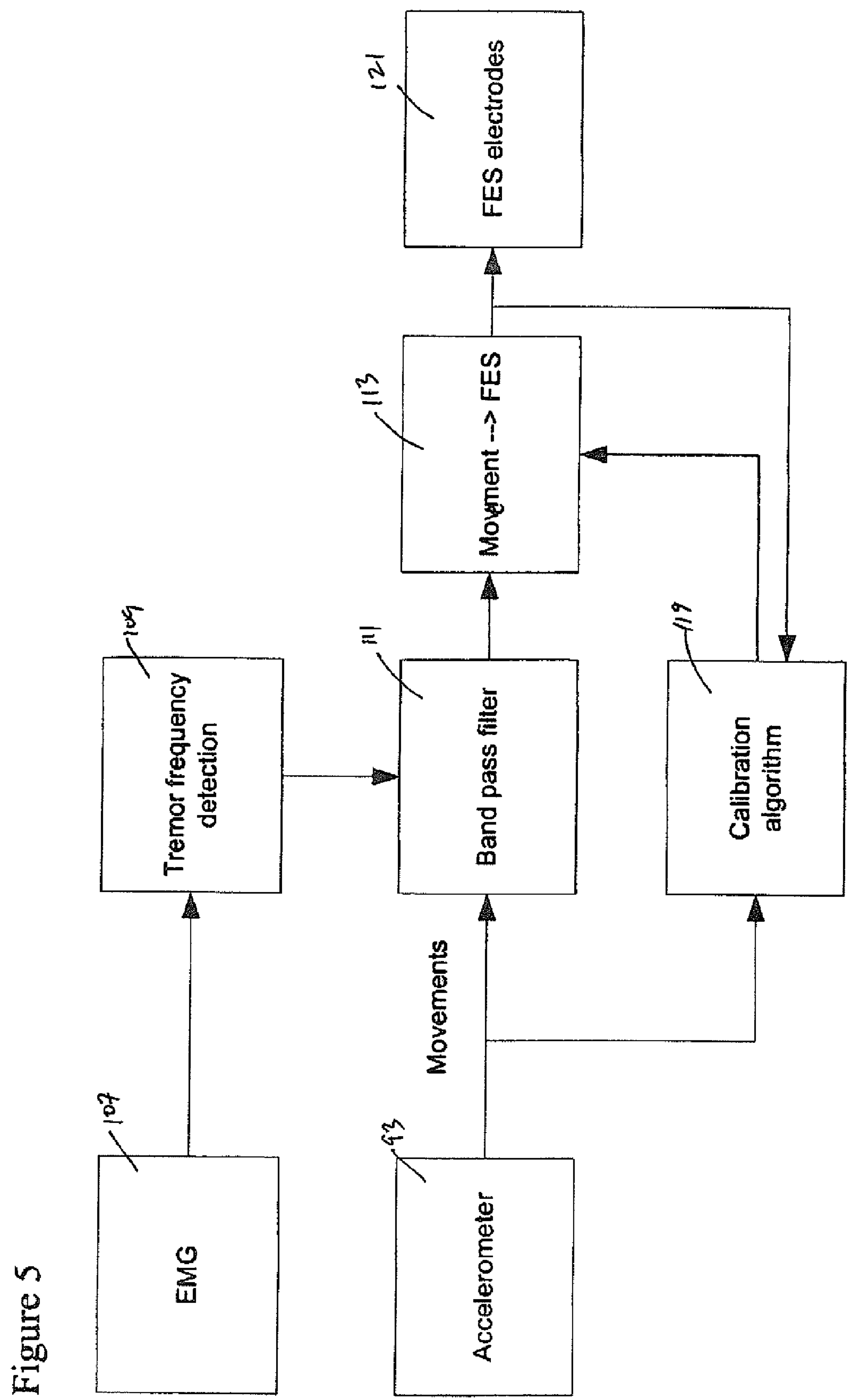
FIG. 5 is a simplified block diagram of a stabilization filter useful in the system of FIG. 1, in accordance with an embodiment of the present invention.

FIG. 5 illustrates a simplified block diagram of a stabilization filter 105 useful in the system of FIGS. 1A-1C, in accordance with an embodiment of the present invention. The stabilization filter 105 may include the EMG 107, whose output is analyzed by a tremor frequency detection module 109. The accelerometer 93 outputs to a band pass filter 111. Movements are measured by the accelerometer 93 and muscle electric activity is measured by the EMG 107. Tremor frequency 117 is detected from EMG 107 signal using peak FFT detection. Movements 113 are band pass filtered 111 around the tremor frequency (usually to [130 Hz]) to ignore slow ("intentional") movements and high frequency noise.

The desired movement is opposite to the sensed movement and the corresponding stimulus at the FES electrodes 121 is calculated using a calibration algorithm 119. Again, FES amplitude is limited for safety.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specifications and which are not in the prior art

REFERENCES

1. Louis E D, Ford B, Lee H, et ale Diagnostic criteria for essential tremor: a population perspective. Arch NeuroI 1998;55(6):823-8

2. Charles P D, Esper G J, Davis T L, et al. Classification of tremor and update on treatment. Am Fam Physician 1999; 59(6):1565-72

3. Wasiclewski P G, Bums J M, Koller W C. Pharmacologic treatment of tremor. Mov Disord 1998; 13 (Suppl 3):90-100.

Tremor statistics

85% of individuals with ET report significant changes in their livelihood and socializing 15% report being seriously disabled by ET 25% changed jobs or took early retirement 65% did not dine out 30% did not attend parties shop alone partake of a favorite hobby or sport or use public transportation 20% stopped driving Author: *Deborah Burke MD,* Consulting Staff Department of Neurology, Largo Diagnostic Clinic Coauthor(s): *Robert A Hauser, MD,* Director, Parkinson 's Disease and Movement Disorders Center, Tampa General Hospital; Professor, Departments of Neurology, Pharmacology, and Experimental Therapeutics, University of South Florida

What is claimed is:

1. A system for enabling self application of anti-tremor means by a disabled patient, the system comprising: a single unit stimulation and recording electrode with an integrated control means; and an alignment application unit which is configured to enable independent application and use by said disabled patient; the alignment application unit having a narrow pathway extending from an outside surface of the alignment application unit to an interior portion of the alignment application unit; an electrode application niche contained in the interior portion of the alignment application unit for placement of the electrode within the alignment application unit; a sensor for sensing muscle movements; and Functional Electrical Stimulation (FES) apparatus for providing FES to a muscle, said FES apparatus being in communication with said sensor via a band pass filter for filtering around a tremor frequency to ignore slow movements and high frequency noise.

2. A method for enabling self application of anti-tremor means by a disabled patient, the method comprising the steps of: providing a single unit stimulation and recording electrode with an integrated control means; providing an alignment application unit which is configured to enable independent application and use by said disabled patient wherein the alignment application unit has a narrow pathway extending from an outside surface of the alignment application unit to an interior portion of the alignment application unit; and placing an electrode application niche in the interior portion of the alignment application unit for placement of the electrode within the alignment application unit, and providing a Functional Electrical Stimulation (FES) apparatus for providing stimulation to a muscle wherein the FES apparatus is able to communicate with the electrode via a band pass filter for filtering around a tremor frequency to ignore slow movements and high frequency noise.

3. The method described in claim 2, the method further comprising the step of: the patient placing an affected body part into the narrow pathway of the alignment application unit.

4. The method described in claim 2, the method further comprising the step of: contacting the single unit stimulation and recording electrode with an affected body part in the interior portion of the alignment application unit.

5. The method described in claim 2, the method further comprising the step of: placing a sensor for sensing muscle movements on the patients affected body part.

6. The method described in claim 2, the method further comprising the step of: attaching the electrode to the external body part of the patient.

7. The method described in claim 2, the method further comprising the step of: removing the electrode by the use of a liquid thereon.

8. The method described in claim 2, the method further comprising the step of: providing a power supply means whereby the electrode may be activated and deactivated by the user when needed.

* * * * *